United States Patent [19]

Inukai et al.

[11] 4,058,665
[45] Nov. 15, 1977

[54] NOVEL 3,15-DILOWER ALKYL PGE$_2$ DERIVATIVES

[75] Inventors: Noriyoshi Inukai; Masuo Murakami, both of Tokyo; Hidenori Iwamoto, Ageo; Isao Yanagisawa; Toshinari Tamura, both of Tokyo; Yoshio Ishii, Omiya; Tetsuya Shizaoki, Misato; Kenichi Tomioka, Kitamoto; Tokuichi Takagi, Tokyo, all of Japan

[73] Assignee: Yamanouchi Pharmaceutical Co., Ltd., Tokyo, Japan

[21] Appl. No.: 629,568

[22] Filed: Nov. 6, 1975

[51] Int. Cl.$^2$ ............................................ C07C 177/00
[52] U.S. Cl. ........................... 560/121; 260/345.7 P; 260/345.8 P; 260/448.8 R; 260/514 D; 542/426; 424/305; 424/317; 560/102; 560/231
[58] Field of Search ....... 260/468 D, 514 D, 448.8 R, 260/240 R, 345.8, 345.7

[56] References Cited

U.S. PATENT DOCUMENTS

| 3,816,393 | 6/1974 | Hayashi et al. | 260/209 |
| 3,878,239 | 4/1975 | Hayashi et al. | 260/514 |

FOREIGN PATENT DOCUMENTS

| 804,898 | 3/1974 | Belgium | 260/468 |
| 116,454 | 9/1975 | Japan | 260/468 |
| 105,633 | 8/1975 | Japan | 260/468 |

*Primary Examiner*—Robert Gerstl
*Attorney, Agent, or Firm*—Burgess, Ryan and Wayne

[57] ABSTRACT

3,15-Dilower alkyl prostaglandin E$_2$ derivatives and 3,15-dilower alkyl prostaglandin D$_2$ derivatives are disclosed. These compounds have antigastric ulcer activity without undesirable side effects to intestinal organs.

8 Claims, No Drawings

NOVEL 3,15-DILOWER ALKYL PGE$_2$ DERIVATIVES

The present invention relates to 3,15-dilower alkyl prostadienoic acid derivatives represented by the general formula:

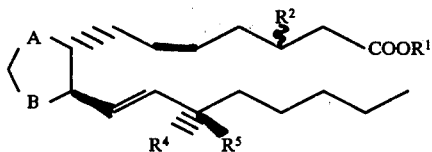

wherein one of A and B represents

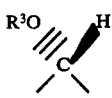

and the other represents

wherein R$^3$ represents a hydrogen atom or a protective group for the hydroxy group, R$^1$ represents a hydrogen atom or a lower alkyl group, R$^2$ represents a lower alkyl group, and one of R$^4$ and R$^5$ represents a free or protected hydroxy group and the other represents a lower alkyl group, and more particularly the present invention relates to 3,15-dilower alkyl prostaglandin E$_2$ (3,15-dilower alkyl PGE$_2$) derivatives represented by the general formula:

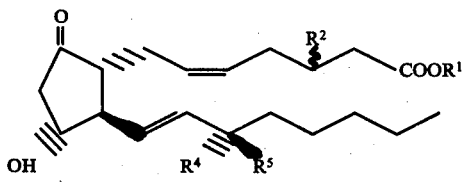

wherein R$^1$, R$^2$, R$^4$ and R$^5$ have the same significance as in general formula LL, and 3,15-dilower alkyl prostaglandin D$_2$(3,15-dilower alkyl PGD$_2$) derivatives represented by general formula:

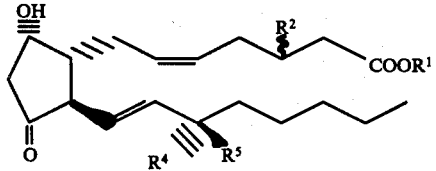

wherein R$^1$, R$^2$, R$^4$ and R$^5$ have the same significance as in general formula II.

Various derivatives of prostanoic acids referred to as prostaglandins are known. These prostaglandins are contained in many aminal's tissues and show a variety of physiological activities. For example, prostaglandin E (PGE) suppresses excessive secretion of gastric juices, so that it is effective for the treatment of ulcers in the stomach and duodenum and the prevention of ulcers. However, when natural prostaglandin is orally administered, its effective period is short and strong side effects are produced, especially, diarrhea caused from excessive promotion of intestine's movement has been often observed, which are most undesirable for administration of prostaglandin. The known prostaglandin derivatives possess the same physiological activities as those of the natural compounds but also exhibit the same side effects as the prostaglandins. There is therefore a great need for prostaglandin derivatives having littler or no side effects, that is, derivatives having a high selectivity in pharmacological activities.

Various attempts for accomplishing the above-mentioned purposes have been made. For example, 15-methyl or 15-ethyl prostaglandin E groups are disclosed in U.S. Pat. Nos. 3,728,328 and 3,812,179. The fact that 15(R)15-methyl prostaglandin E$_2$ methyl ester has strong anti-ulcer activity has been known [Prostaglandins, 5, (5) 455-463 (1974)]. However, it has been found that these compounds cause very severe diarrhea as a side effect. Such diarrhea is one of severe undesired side effects for administering prostaglandins for long periods, and the compounds which do not possess such diarrhea action have been desired.

The present inventors have found after various studies, compounds which have superior anti-ulcer activities and little or no diarrhea effect.

The compounds of this invention are novel and have high selectivity in pharmacological activities as compared with natural or synthetic prostaglandin derivatives, and are expected to be applicable as medicaments.

In general formula II of the desired compounds in this invention, practical examples of the lower alkyl group are an alkyl group having 1 to 4 carbon atoms such as a methyl group, an ethyl group, an isopropyl group, a butyl group, etc., preferably an alkyl group having 1 or 2 carbon atoms, and practical protective groups for the hydroxy group are the groups which can be removed under mild conditions, such as a tetrahydropyran-2-yl group, a trilower alkyl silyl group, such as a timethylsilyl group or a triethylsilyl group; or a triphenysilyl group; or an acyl group such as an acetyl group, a propionyl group or a p-phenylbenzoyl group.

The preferred compounds prepared in this invention are as follows:

11α,15(S)-dihydroxy-3,15-dimethyl-9-oxo-5(cis), 13(trans)-prostadienoic acid (3,15-dimethyl PGE$_2$), 11α,15(R)-dihydroxy-3,15-dimethyl-9-oxo-5(cis),13(-trans)-prostadienoic acid (3,15-dimethyl-15-epi PGE$_2$), 11α,15(S)-dihydroxy-3,15-dimethyl-9-oxo-5(cis),13(-trans)-prostadienoic acid methyl ester (3,15-dimethyl PGE$_2$ methyl ester), 11α,15(R)-dihydroxy-3,15-dimethyl-9-oxo-5(cis),13(-trans)-prostadienoic acid methyl ester (3,15-dimethyl-15-epi PGE$_2$ methyl ester), 11α,15(S)-dihydroxy-3,15-diethyl-9oxo-5(cis),13(trans)-prostadienoic acid (3,15-diethyl PGE$_2$), 11α,15(R)-dihydroxy-3,15-diethyl-9-oxo-5(cis),13(-trans)-prostadienoic acid methyl ester (3,15-diethyl-15-epi PGE$_2$ methyl ester) and 11α,15(R)-dihydroxy-3,15-dimethyl-9-oxo-5(cis),13(-trans)-prostadienoic acid ethyl ester (3,15-dimethyl-15-epi PGE$_2$ ethyl ester), etc., and as compound II", 9α,15(S)-dihydroxy-3,15-dimethyl-11-oxo-5(cis),13(-trans)-prostadienoic acid (3,15-dimethyl PGD$_2$), 9α,15(R)-dihydroxy-3,15-dimethyl-11-oxo-5(cis),13(-trans)-prostadienoic acid (3,15-dimethyl-15-epi $PGD_2$), 9α,15(S)-dihydroxy-3,15-dimethyl-11-oxo-5(cis),13(-trans)-prostadienoic acid methyl ester (3,15-dimethyl $PGD_2$ methyl ester), 9α,15(R)-dihydroxy-3,15-dimethyl-11-oxo-5(cis),13(-trans)-prostadienoic acid methyl ester (3,15-dimethyl-15-epi $PGD_2$ methyl ester), 9α,15(S)-dihydroxy-3,15-dimethyl-11-oxo-5(cis),13(-trans)-prostadienoic acid ethyl ester (3,15-dimethyl $PGD_2$ ethyl ester), 9α,15(R)-dihydroxy-3,15-diethyl-11-oxo-5(cis),13(-trans)-prostadienoic acid ethyl ester (3,15-diethyl-15-epi $PGD_2$ ethyl ester), etc.

Further, as examples of the present compounds, there are the compounds having a protective group which can be easily removed for the hydroxy group of the above-mentioned compounds and/or the compounds having a free carboxy group, and pharmacologically acceptable salts, for example, sodium salt, potassium salt, ammonium salt, aluminum salt, calcium salt, diethanolamine salt, lysine salt, arginine salt, etc.

In the aforesaid formulae I, II, II' and II'', the dotted line attached to the cyclopentane ring means that there is an alpha steric configuration, that is, there is positioned the substituent below the plane of the cyclopentane ring and the heavy line attachment means that there is a beta steric configuration, that is, there is positioned the substituent above the plane of the cyclopentane ring. Furthermore, the wavy line attached to the side chain means that there is an S steric configuration or an R steric configuration or a mixture thereof.

The starting materials I used in this invention are represented by the general formula

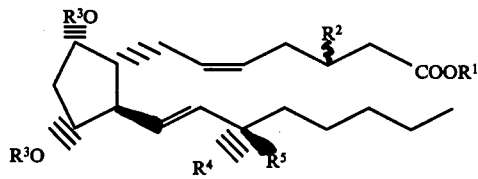

I wherein $R^1$, $R^2$, $R^4$ and $R^5$ have the same significance as in formula II, and $R^3$ represents hydrogen, as a protective group and at least one of the two $R^3$ groups is hydrogen, and can be prepared, for example, by the process disclosed in the Japanese patent application which has been laid open to the public as No. 50-105633.

In compound I, for introducing a protective group to the compound having free hydroxy groups at 9 or 11 and/or 15 position, the compound is reacted with, for example, 2,3-dihydropyran in the in the presence of catalytic amount of acid such as p-toluene sulfonic acid in an inert solvent such as dichloromethane.

For introducing trilower alkyl silyl group, triphenylsilyl group or acyl group, the compound is reacted with the halide compounds such as chloride, bromide of these groups in the presence of a tertiary amine such as pyridine, triethylamine or hexamethylsilazane etc., in an inert solvent such as chloroform, ethylenechloride, benzene or the mixture thereof. Excessive amounts of pyridine may be used both as tertiaryamine and solvent. Further, when introducing trimethylsilyl group, trimethylsilyl diethylamine can be used as a reagent.

The desired compounds in this invention are prepared by reacting compound I with an oxidizing agent. Practically useful oxidizing agents are Jones reagent, that is, acidic chromic acid, for example, a mixture of chromic anhydride and sulfuric acid (The Merck Index, 8th Ed. 1182) and a Collin's reagent (a complex of chromic anhydride and pyridine; Tetrahedron Letters, 3363 (1968), J. Am. Chem. Soc., 75, 422 (1953)), a mixture of sulfur trioxides in pyridine and diemthylsulfoxide (J. Am. Chem. Soc., 89, 5505, (1967)) and a mixture of dicyclohexylcarbodiimide and dimethylsulfoxide (J. Am. Chem. Soc., 87, 5661, (1965)).

In the case of using the Jones reagent as the oxidizing agent, it is preferred to dissolve the compound I in a solvent such as acetone and after adding thereto with stirring the Jones reagent in an amount slightly larger than the theoretical amount under cooling. In the case of using the Collin's reagent as the oxidizing agent, it is preferred to dissolve the compound I in a solvent such as methylene chloride and after adding thereto the Collin's reagent, to react at room temperature or under cooling. The reaction is usually complete in 5 to 20 minutes. The remaining oxidizing agent in a reaction mixture is destroyed, for example by adding a lower alcohol such as isopropanol.

When the obtained compounds have a protective group for a hydroxy group and when its removal is desired, it can be carried out by many conventional methods according to the properties of a protective group. For example, when a protective group is a trilower alkyl silyl group or a triphenylsilyl group, the removal of the protective group is conducted by adding the compound in a mixture of water and an organic solvent.

The removal of a protective group is accelerated by adding a catalytical amount of an acid. The period of reaction is determined by temperature, and at about 25° C the reaction is sufficiently completed in a few hours.

When the protective group is an acyl group, it is preferred to remove the protective group in a mixture of alkalimetal carbonate in a suitable solvent such as water and/or alcohol. When the protective group is a tetrahydropyran-2-yl group, it is preferred to remove a protective group at temperatures of about 40°-55° C in methanolic hydrochloric acid or aqueous tetrahydrofuran solution containing acetic acid.

The desired compounds thus obtained are isolated and purified by conventional methods used in the field of prostaglandin such as extraction and column chromatography, etc.

Experiment

Each of ten male Sprague-Dawly rate, 12 weeks old, in one group was isolated in a cage with a large mesh wire net at the bottom during experimental period and prevented from coprophagia. During this period the animals were completely fasted for 48 hours and water was provided only for 32 hours from the beginning. The animal was anesthetized with ether, the pylorus was ligated through a short midline incision. The samples were administered with a gastric tube immediately after the ligation. The animals were sacrificed 21 hours later with chloroform and their abdomens were widely opened to take out the stomach. The stomach was opened for inspection of ulcers.

Each of five male Sprague-Dawly rats, 12 weeks old, in one group was fasted for 24 hours. The samples were administered with a gastric tube, and the occurrence of diarrhea was observed in the following 24 hours.

The results are given in the following table.

| Compound | ED$_{50}$ ($\mu$g/Kg, p.o) | | b)/a) |
|---|---|---|---|
| | a) antiulcer activity | b) diarrhea activity | |
| A 11α, 15(R)-dihydroxy-15-methyl-9-oxo-5(cis),13(trans)-prostadienoic acid methyl ester | 98(59–162) | 120(56–258) | 1.2 |
| B 11α, 15(S)-dihydroxy-15-methyl-9-oxo-5(cis), 13(trans)-prostadienoic acid methyl ester | 60(30–119) | 47 (24–92) | 0.8 |
| C 11α, 15(R)-dihydroxy-3,15-dimethyl-9-oxo-5(cis), 13 (trans)-prostadienoic acid methyl ester | 200(95–420) | 1200 (755–1908) | 6.0 | note:
Figures in parenthesis indicate confidence limit.
Compounds A and B are known compounds (cf. U.S. Pat. 3,728,328).
Compound C was prepared in Example 4 of the present invention.

As is clear from the above results, the compounds of this invention have superior antiulcer activity without diarrhea than those of known compounds.

The compounds of this invention have superior pharmacological activities on oral administration and are administered in a form of tablet, capsule or syrup with a conventional pharmaceutical carrier. When administered to human beings, it is preferred to administer the amount of 200—300 $\mu\mu$g daily.

EXAMPLE 1

In 18 ml of acetone was dissolved 50.7 mg of 9α,11α, 15(S)trihydroxy-3,15-dimethyl-5(cis),13(trans)-prostadienoic acid and after cooling the solution to temperatures between −35° C and −40° C, 0.036 ml of a Jones reagent (prepared by mixing 4.2 g of chromic anhydride, 3,4 ml of concentrated sulfuric acid, and 12 ml of water) cooled to temperatures lower than 0° C was added to the solution with stirring. The mixture was futher stirred for 30 minutes at temperatures between −35° C and −40° C and after further adding thereto 0.01 ml of the Jones reagent cooled, the resultant mixture was further stirred for 15 minutes at the same temperature.

To the reaction mixture was added 0.3 ml of isopropyl alcohol and after stirring the mixture for 10 minutes at temperatures between −35° C and −40° C, the insoluble materials were filtered off with the aid of Perlite. The filtrate was concentrated under reduced pressure at 0° C, the residue was dissolved in 50 ml of methylene chloride, and then the solution was washed three times each time with 4 ml of saturated aqueous sodium chloride solution. The solution was dried over anhydrous magnesium sulfate and then the solvent was distilled off under reduced pressure to provide 52 mg of an orange oily material. The oily material was subjected to a silica gel column chromatography and then using a mixture of ethyl acetate, methanol, and acetic acid (100:2:1 in volume ratio) as an eluant, 4.6 mg of 11α, 15(S)dihydroxy-3,15-dimethyl-9-oxo-5(cis), 13(trans)-prostadienoic acid and 20.5 mg of 9α, 15(S)-dihydroxy-3,15-dimethyl-11-oxo-5(cis), 13 trans-prostadienoic acid were obtained.

[α] $_D^{21}$ −114.7 (C=0.35, chloroform) in the former
[α] $_D^{21}$ −2.95 (C=0.61, chloroform) in the latter

EXAMPLE 2

By following the similar reaction, treatment and purification of Example 1 using 25.6 mg of 9α, 11α, 15(R)-trihydroxy-3,15-dimethyl-5(cis),13(trans)-prostadienoic acid, 3 mg of 11α, 15(R)-dihydroxy-3,15-dimethyl-9-oxo-5(cis), 13(trans)-prostadienoic acid and 15.1 mg of 9α, 15(R)-dihydroxy-3,15-dimethyl-11-oxo-5(cis),13(-trans)-prostadienoic acid were obtained.

[α] $_D^{18}$ −75.0 (C = 0.2, chloroform) in the former
[α] $_D^{18}$ −15.3 (C= 0.66, chloroform) in the latter.

EXAMPLE 3

In 1.8 ml of dry acetone was dissolved 56.3 mg of 9α, 11α, 15(S)-trihydroxy-3,15-dimethyl-5(cis),13(trans)-prostadienoic acid methyl ester and while cooling the solution to temperatures between −40° C and −45° C in nitrogen stream, 1.5 ml of trimethylsilyl diethylamine was added to the solution with stirring followed by stirring further 2 hours at temperatures between −40° C and −45° C in nitrogen stream. Then, 0.5 ml of methanol was added to the solution and after mixing the mixture for 20 minutes at temperatures between −40° C and −45° C and then for 20 minutes at 0° C, the solvent was distilled off under reduced pressure at 0° C to give 77.3 mg of a yellow oily material.

The oily material was dissolved in 3 ml of methylene chloride and the solution was added with stirring in a nitrogen stream to the cooled (0° C) Collin's reagent solution prepared by reacting 128.5 mg of chromic anhydride and 203 mg of pyridine in 5 ml of methylene chloride. Thereafter, the reaction was carried out for 5 minutes at 0° C and then for 5 minutes at room temperature. The reaction mixture obtained was cooled to 0° C and after adding thereto 3 ml of isopropyl alcohol, the mixture was stirred for 10 minutes. The insoluble materials were filtered away and the solvent was distilled off from the filtrate under reduced pressure. To the residue was added ether and after filtering away insoluble materials, the solvent was distilled off from the filtrate under reduced pressure to provide 55.3 mg of a dark yellow oily material.

The oily material thus obtained was dissolved in 3 ml of methanol and after adding 1 ml of water and 5 drops of acetic acid to the solution, the mixture was stirred for 30 minutes at room temperature. Then, by distilling off the solvent from the mixture under reduced pressure, 48.7 mg of a dark oily material was obtained. The oily material was subjected to a silica gel column chromatography and using a mixture of ethyl acetate and n-hexane, (2:1 in volume ratio) as an eluant, 19.9 mg of 11α, 15(S)-dihydroxy-3,15-dimethyl-9-oxo-5(cis),13(trans)-prostadienoic acid methyl ester and 8.1 mg of 9α, 15(S)-dihydroxy-3,15-dimethyl-11-oxo-5(cis),13(trans)-prostadienoic acid methyl ester were obtained.

[α] $_D^{22}$ −88.7 (C = 0.66), chloroform) in the former $[\alpha]_D^{22}$ −3.27 (C = 0.52, chloroform) in the latter.

EXAMPLE 4

By following similarly the procedure of Example 3 using 33.7 mg of 9α, 11α, 15(R)-trihydroxy-3,15-dimethyl-5(cis),13(trans)-prostadienoic acid methyl ester, 13.6 mg of 11α, 15(R)-dihydroxy-3,15-dimethyl-9-oxo-5(cis), 13(trans)-prostadienoic acid methyl ester and 4.2 mg of 9α, 15(R)-dihydroxy-3,15-dimethyl-11-oxo-5(cis),13(trans)-prostadienoic acid methyl ester were obtained.

$[\alpha]_D^{22}$ −74.7 (C = 0.9, chloroform) in the former
$[\alpha]_D^{22}$ −7.15 (C = 0.28, chloroform) in the latter.

We claim:

1. 3,15-dilower alkyl prostadienoic acid derivatives represented by the formula

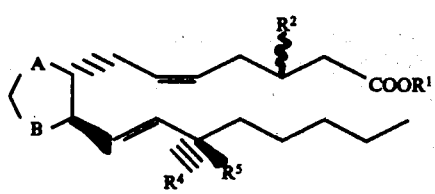

wherein B represents

and A represents

and $R^3$ represents a hydrogen atom or a protective group selected from the group consisting of a tetrahydropyran-2-yl group, a trilower alkyl silyl group, a triphenylsilyl group, an acetyl group, a propionyl group, and a p-phenylbenzoyl group, $R^1$ represents a hydrogen atom or a lower alkyl group, $R^2$ represents a lower alkyl group, and one of $R^4$ and $R^5$ represents a free hydroxyl group or a hydroxyl group protected by a protective group as defined with reference to $R^3$ and the other represents a lower alkyl group.

2. A compound according to claim 1, wherein $R^3$ represents an acetyl or a propionyl group.

3. A compound according to claim 1, wherein the trilower alkyl silyl group is a trimethylsilyl or a triethylsilyl group.

4. A compound, according to claim 1, which is 3,15-dilower alkyl prostaglandin $E_2$ derivatives represented by the formula

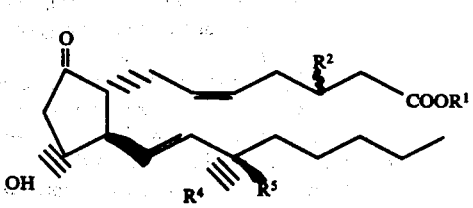

wherein $R^1$, $R^2$, $R^4$ and $R^5$ have the same significance as in claim 1.

5. A compound, according to claim 1, which is 11α,15(S)-dihydroxy-3,15-dimethyl-9-oxo-5(cis),13(trans)-prostadienoic acid.

6. A compound, according to claim 1, which is 11α, 15(R)-dihydroxy-3,15-dimethyl-9-oxo-5(cis),13(trans)-prostadienoic acid.

7. A compound, according to claim 1, which is 11α,15(S)-dihydroxy-3,15-dimethyl-9-oxo-5(cis),13(trans)-prostadienoic acid methyl ester.

8. A compound, according to claim 1, which is 11α,15(R)-dihydroxy-3,15-dimethyl-9-oxo-5(cis),13(trans)-prostadienoic acid methyl ester.

* * * * *

UNITED STATES PATENT OFFICE
CERTIFICATE OF CORRECTION

Patent No. 4,058,665  Dated November 15, 1977

Inventor(s) Noriyoshi Inukai, et al

It is certified that error appears in the above-identified patent and that said Letters Patent are hereby corrected as shown below:

Column 1, line 48: "LL" should be --II--.

line 62: "prostanoic" should be --prostadienoic--.

Column 2, line 10: "littler" should be --little--.

line 41: "timethylsi-" should be --trimethylsi- --.

line 42: "triphenysilyl" should be --triphenylsilyl--.

Column 5, line 26: Delete "$\mu$" (1st occurrence).

line 34: "3,4" should be --3.4--.

Signed and Sealed this

Ninth Day of May 1978

[SEAL]

Attest:

RUTH C. MASON
Attesting Officer

LUTRELLE F. PARKER
Acting Commissioner of Patents and Trademarks